United States Patent [19]  
Romesser

[11] 4,431,736  
[45] Feb. 14, 1984

[54] PHENYLHYDROQUINONE FROM BIPHENYL BY BIOTRANSFORMATION WITH SELECTED FUNGI

[75] Inventor: James A. Romesser, Wilmington, Del.

[73] Assignee: E. I. Du Pont de Nemours and Company, Wilmington, Del.

[21] Appl. No.: 383,456

[22] Filed: Jun. 1, 1982

[51] Int. Cl.$^3$ .......................... C12P 7/22; C12R 1/645
[52] U.S. Cl. ..................................... 435/156; 435/911
[58] Field of Search ......................... 435/156, 171, 911

[56] References Cited

U.S. PATENT DOCUMENTS 3,392,171  7/1968  Fonken et al. ...................... 435/911
4,153,509  5/1979  Schwartz ............................ 435/156

FOREIGN PATENT DOCUMENTS 54-151195  11/1979  Japan ..................................... 435/156

OTHER PUBLICATIONS

Schwartz et al., Appl. Environ. Microbiol., 39, pp. 702 to 708 (1980).
Herber et al., C. R. Soc. Biol., 163, pp. 1657 to 1661 (1969).
Dodge et al., Biochem J., 178, pp. 223 to 230 (1979).
Herber et al., Chem. Abstracts, 79, 666c (1973).
Smith et al., Arch. Biochem. Biophys., 161, pp. 551 to 558 (1974).
Smith et al., J. Appl. Bacteriol., 49, pp. 65 to 73 (1980).
Kieslich, "Microbial Transformations of Non-Steroid Cyclic Compounds", John Wiley & Sons, 1976, p. 512.

*Primary Examiner*—Esther M. Kepplinger

[57] ABSTRACT

Microbiological oxidation of biphenyl to bis-hydroxylated biphenyl employing *Thamnostylum piriforme*.

7 Claims, No Drawings

PHENYLHYDROQUINONE FROM BIPHENYL BY BIOTRANSFORMATION WITH SELECTED FUNGI

BACKGROUND OF THE INVENTION

This invention concerns the microbiological oxidation of biphenyl to 2,5-dihydroxybiphenyl(phenylhydroquinone) employing the fungus *Thamnostylum piriforme* (including species formerly known as *Helicostylum piriforme*).

Microbiological oxidation of biphenyls by a variety of bacteria and fungi has been studied. For instance:

U.S. Pat. No. 4,153,509 and Schwartz et al., Appl. Environ. Microbiol., 39, pages 702 to 708 (1980) disclose the microbiological oxidation of a biphenyl compound with a microorganism of the genus Absidia and certain species of Aspergillus and Cunninghamella. Products obtained are mono- and dihydroxybiphenyls which contain a hydroxyl group in each ring, e.g., 4-hydroxybiphenyl and 4,4'-dihydroxybiphenyl.

Japanese Application No. 54-151195 discloses a process for the preparation of p-phenylphenol and m-phenylphenol by microbiological oxidation of biphenyl by the bacterium, Pseudomonas.

Herber et al., C. R. Soc. Biol., 163, pages 1657 to 1661 (1969), disclose metabolism of 2-hydroxybiphenyl (o-phenylphenol) and its conversion to a mixture of polyhydroxyl biphenyls including 2,5-dihydroxybiphenyl by a fungus, Mucor.

Dodge et al., Biochem J., 178, pages 223 to 230 (1979), disclose formation of 2,5-dihydroxybiphenyl by microbiological oxidation of 2-hydroxybiphenyl by the fungus *Cunninghamella elegans*. The compound, 2,5-dihydroxybiphenyl was not obtained directly from biphenyl.

Herber et al., Chem. Abstracts, 79, 666c (1973), disclose the metabolic conversion of thymol and carvacrol into thymohydroquinone, and the conversion of 2-hydroxybiphenyl into 2,5-dihydroxybiphenyl by *Mucor hiemalis*.

Smith et al., Arch. Biochem. Biophys., 161, pages 551 to 558 (1974), disclose aromatic hydroxylation of biphenyl to 2-hydroxybiphenyl and 4-hydroxybiphenyl by *Helicostylum piriforme*.

Smith et al., J. Appl. Bacteriol., 49, pages 65 to 73 (1980), disclose use of *Heliocostylum piriforme* to produce 2-hydroxybiphenyl. *Aspergillus niger* and *Cunninghamella echinulata* were reported to give small amounts of 2,5-dihydroxybiphenyl in addition to major amounts of other hydroxylated products.

Kieslich, "Microbial Transformations of Non-Steroid Cyclic Compounds," John Wiley & Sons, 1976, page 512, discloses microbial transformation of biphenyl to hydroxylated biphenyls including 2,3-dihydroxybiphenyl using the bacterium *Pseudomonas putida* and an unspecified gram negative bacterium.

SUMMARY OF THE INVENTION

This invention concerns a method for making 2,5-dihydroxybiphenyl by contacting biphenyl with at least one fungal microorganism selected from the species *Thamnostylum piriforme*, in the presence of a source of organic nitrogen, the weight ratio of biphenyl to dry cells of the microorganism being less than about 0.031 to 1.

The one-step oxidation reaction of this invention is preferably carried out at ambient temperatures and at atmospheric pressures. The product, 2,5-dihydroxybiphenyl, is an intermediate in the formation of polyester condensation polymers made by reaction of the 2,5-dihydroxybiphenyl compound with a suitable dibasic acid. Such polymers, particularly those prepared from aromatic dibasic acids, have high strength and heat resistance.

The preferred strains of microorganism for the process of this invention are Thamnostylum piriforme QM 6945 (formerly known as *Helicostylum piriforme* QM 6945) obtainable from Northern Utilization Research and Development Division, U.S. Department of Agriculture, Peoria, IL 61604 and *Thamnostylum piriforme* 8992 available from American Type Culture Collection, 12301 Parklawn Drive, Rockville, MD 20852.

It is preferred that the microorganism be cultivated in a suitable medium prior to contacting with the biphenyl reactant. In this preferred embodiment, organic nitrogen need not be present during cultivation of the microorganism but must be present during conversion of the biphenyl to 2,5-dihydroxybiphenyl. Alternatively, the microorganism can be cultivated in the presence of the biphenyl reactant, in which instance organic nitrogen must be present at all times. The medium to be used for the cultivation of the microorganism can by any of the usual media commonly employed for cultivation of microorganisms.

The concentration of biphenyl reactant is critical relative to the concentration of microorganism(s). To obtain significant quantities of the desired 2,5-dihydroxybiphenyl, it has been found necessary that the weight ratio of biphenyl to dry cells of the microorganism be less than about 0.031 to 1, and preferably no greater than 0.028 to 1.

DETAILS OF THE INVENTION

A typical medium in which the microorganism(s) can be cultivated includes a carbon source, a nitrogen source, deionized water, a buffer for control of pH, and optionally, inorganic salts. Suitable carbon sources include assimilable aliphatic carbon compounds, such as glucose, maltose, fructose, sucrose, xylose, acetate, and butyrate. Suitable nitrogen sources include inorganic nitrogen compounds, organic nitrogen compounds, and mixtures thereof. Illustrative of useful inorganic nitrogen compounds are ammonium chloride, ammonium nitrate, ammonium sulfate, ammonium phosphate and the like. Useful organic nitrogen compounds include peptone, neopeptone, soytone, tryptone, corn, yeast extract, soybean powder and the like. Useful buffers include amino acids which are components of the peptones, disodium hydrogen phosphate, potassium dihydrogen phosphate, and the like.

Although the microorganism(s) can be grown with an inorganic nitrogen compound as the sole nitrogen source, a suitable organic nitrogen source such as peptone, neopeptone, soytone, or tryptone is necessary in the medium for conversion of biphenyl to 2,5-dihydroxybiphenyl. As an optional component, the culture medium can also include one or more inorganic salts and one or more trace elements. For the inorganic salt component, sodium chloride, potassium phosphate, sodium sulfate, iron sulfate, magnesium sulfate, and manganese sulfate can be used. For the trace elements, boric acid; copper and zinc sulfate; copper chloride; and/or the hydrochloride compound(s) of magnesium, iron, manganese, cobalt, zinc and copper can be used.

The biphenyl reactant can be added to the microorganism(s) in culture at any time between the beginning of microorganism growth and the end of microorganism growth. Biphenyl can also be added after the microorganism has been concentrated and redeposited into the same culture medium or, alternatively, a different culture medium. Biphenyl can be added to the reaction mixture neat or dissolved in a suitable solvent such as ethanol, methanol, dimethylformamide, and the like.

After addition of the biphenyl reactant, the process is effected for a period of time sufficient to produce the desired dihydroxybiphenyl compound. In general, residence times vary from about one day to twenty days or longer. Sufficient time must be allowed for formation of the individual enzymes required for conversion of biphenyl to 2,5-dihydroxybiphenyl. However, separation of the reaction product should be effected before significant metabolism (degradation) takes place. It should be appreciated that reaction times are influenced to a significant degree by pH, reaction temperature, the concentration and choice of microorganisms, the concentration of reactant, and other factors known to those skilled in the art.

After the process of this invention has gone to completion, the desired product can be collected in pure form by conventional methods. Thus, for example, the mycelium can be removed from the water/product by filtration and the product collected using gas chromotography, extraction, thin layer chromotography, distillation and the like.

The concentration of the microorganism required to effect the process of the invention is not critical. In preferred embodiments, the microorganism concentration will be at least about 0.5 percent based on the weight of the reaction mixture. The pH of the process medium can vary from about 4.0 to 7.5, but it is preferably in the range of 6.0 to 6.5 for optimum conversion to product. The reaction temperature is generally about 17° to 33° C., and preferably 26° to 28° C. for optimum conversion to product.

The Examples illustrate the process of this invention, Example 2 representing a preferred embodiment. All parts and percentages are by weight, and all degrees are Celsius unless otherwise noted.

GENERAL PROCEDURE

Three types of culture media were used. Their compositions are described in Table 1. Before inoculation, the media were sterilized by autoclaving for 15 minutes at a gauge pressure of 103 kPa.

Sterilized potato dextrose agar (Medium B) was added to sterilized glass bottles (40 mm×160 mm×40 mm). The medium was inoculated with microorganisms which were then allowed to grow at 25° for 2 to 10 weeks. A suspension of fungal spores was made by adding 10 ml of 0.1 M $KPO_4$ buffer (pH 5.0 and containing 0.01% (vol/vol) of a polyoxyethylene sorbitan mono-oleate surface active agent) to the bottle. The spores were dislodged from the mycelial mat with a sterile glass rod. Growth was initiated in 50 ml of medium by the addition of 0.5 ml of spore suspension. The culture was incubated at 30° with shaking. After 2 to 3 days, the cells (pellets or dispersed short filaments) were decanted into sterile 50 ml polypropylene centrifuge tubes and pelleted by centrifugation at maximal speed on a clinical centrifuge. The growth medium was decanted from the tube and discarded.

The cells were then resuspended in 25 ml of the designated medium to be used, and they were returned to their growth flask. Biphenyl (3.0 mg), dissolved in 50 µl of dimethylformamide, was added to the cell suspension and the flasks were returned to the shaker at 30°. The quantity of biphenyl added gave a concentration of about 0.021 mg of biphenyl per mg of dry cell weight. After incubation for the desired time, the biooxidation reaction was stopped by cooling the flask to 4°.

Prior to extraction of the aromatic products, the mycelia were removed from the medium by filtration through coarse sintered glass. Two 25 ml aliquots of ethyl acetate were used to extract the cells and the growth medium, respectively. The ethyl acetate fractions were combined, dried over anhydrous sodium sulfate, and the solvent was removed by flash evaporation. The residue was dissolved in 100 µl of acetone, then 100 µl toluene was added. A 100 µl aliquot of this solution was transferred to a 1.0 ml vial and 100 µl of acetonitrile containing 0.1 mg of α-naphthol (internal standard) was added. After the addition of 25 µl of heptafluorobutyric anhydride (HFBA), the vial was closed and heated at 65° for 2 hr to complete the conversion of hydroxylated products to the corresponding esters.

A gas chromatographic procedure was used to determine the amount and identity of hydroxylated biphenyls formed. An aliquot of the solution of esters derived from HFBA was injected onto a column of 3% silicone on acid-washed diatomaceous earth (100 to 120 mesh, 6'×2 mm ID stainless steel) in a Perkin-Elmer Sigma II gas chromatograph. The carrier gas was helium at 40 ml/min, and products were detected by a flame ionization detector. The temperature program used was: 120° for 11 min, then 3°/min rise to 150°, and held 4 min at 150°. Injector and detector were operated at 200°. The amount of phenols were determined by measuring the ratio of the phenol peak area to the peak area of the α-naphthol internal standard. Identity of the hydroxylated biphenyls was determined by comparing the retention times of the unknowns to authentic samples. Identities were confirmed by mass spectrometry.

TABLE 1

| Component | Amount |
|---|---|
| Medium A. Sabauroud Dextrose Broth (SDB) | |
| A. Neopeptone | 10 g |
| B. Glucose | 20 g |
| C. Deionized water | 1 liter |
| pH 5.7 | |
| Medium B. Potato Dextrose Agar | |
| A. Infusion from potatoes | 200 g |
| B. Glucose | 20 g |
| C. Agar 15 g | |
| D. Deionized water | 1 liter |
| pH 5.6 | |
| Medium C. | |
| A. $Na_2HPO_4$ | 0.6 g |
| B. $KH_2PO_4$ | 5.4 g |
| C. $NH_4NO_3$ | 3.0 g |
| D. Solution containing: | 20 ml |
| 1. 10 g of nitrilotriacetic acid | |
| 2. 7.3 g of KOH | |
| 3. 14.45 g of $MgSO_4$ | |
| 4. 3.34 g of $CaCl_2.2H_2O$ | |
| 5. 0.009 g of $(NH_4)_6Mo_7O_{24}.4H_2O$ | |
| 6. 0.099 g of $FeSO_4.7H_2O$ | |
| 7. 0.05 g of nicotinic acid | |
| 8. 0.025 g of thiamine hydrochloride | |
| 9. 0.0005 g of biotin | |
| 10. 50 ml of a solution containing: | |

TABLE 1-continued

| Component | Amount |
|---|---|
| Medium A. Sabauroud Dextrose Broth (SDB) | |
| a. 0.25 g of ethylenediaminetetraacetic acid | |
| b. 1.095 g of $ZnSO_4.7H_2O$ | |
| c. 0.5 g of $FeSO_4.7H_2O$ | |
| d. 0.154 g of $MnSO_4.H_2O$ | |
| e. 0.039 g of $CuSO_4.5H_2O$ | |
| f. 0.025 g of $Co(NO_3)_2.6H_2O$ | |
| g. 0.018 g of $Na_2B_4O_7.10H_2O$ | |
| h. 1 liter of deionized water | |
| 11. 1 liter of deionized water | |
| E. Glucose | 40 g |
| F. Tryptone | 10 g |
| G. Deionized water | 1 liter |

EXAMPLES 1 TO 4

The General Procedure was employed in each of these Examples, and the results are summarized in Table 2. In each Example, the designated microorganism was grown in Medium B, and the biooxidation of biphenyl was carried out in the designated medium.

TABLE 2

| | | | | Biphenyl Hydroxylation Products, µg/mL | |
|---|---|---|---|---|---|
| Ex. | Micro-organism | Medium | Incubation Time, Days | o-Phenyl-phenol | Phenyl-hydro-quinone |
| 1 | a | A | 2.8 | 2.6 | 7.1 |
| 2 | a | A | 3.9 | 7.9 | 43.4 |
| 3 | a | C | 2.1 | 35.4 | 8.1 |
| 4 | b | A | 2.0 | 60.2 | 4.5 | a = Thamnostylum piriforme QM 6945;
b = Thamnostylum piriforme 8992.

EXAMPLES 5 TO 7

These Examples demonstrate the effect of biphenyl concentration on phenylhydroquinone formation. The general procedure was employed using *Thamnostylum piriforme* QM6945 as the microorganism in Medium A. A transformation period of 3.0 days was employed with approximately 183 mg of dry cell weight at the time of biphenyl addition. The results, summarized in Table 3, show that a weight ratio of biphenyl to dry cells of the microorganism of less than 0.033 to 1, i.e., about 0.031 to 1, is required for significant production of phenylhydroquinone.

TABLE 3

| Ex. | Biphenyl, mg | Biphenyl/ Dry Cell Wt. Ratio | Cell Biomass Increase, mg | Phenyl-hydro-quinone, mg | o-Phenyl-phenol, mg |
|---|---|---|---|---|---|
| 5 | 1.5 | 0.0082 | 268 | 0.21 | 0.052 |
| 6 | 3.0 | 0.016 | 172 | 0.22 | 0.082 |
| 7 | 4.5 | 0.025 | 73 | 0.0030 | 0.17 |
| Comparison A | 6.0 | 0.033 | 0 | None detected | 0.027 |
| Comparison B | 7.5 | 0.041 | 2 | None detected | 0.014 |

The embodiments of the invention in which an exclusive property or privilege is claimed are defined as follows:

1. A method for making 2,5-dihydroxybiphenyl comprising contacting biphenyl with at least one fungal microorganism selected from *Thamnostylum piriforme*, in the presence of a source of organic nitrogen, the weight ratio of biphenyl to dry cells of microorganism being less than about 0.031 to 1.

2. A method according to claim 1 wherein the microorganism is *Thamnostylum piriforme* NRRL QM6945.

3. A method according to claim 1 wherein the microorganism is *Thamnostylum piriforme* ATCC 8992.

4. A method according to claim 1 wherein the concentration of the microorganism is at least about 0.5 percent based on the weight of the reaction mixture.

5. A method according to claim 1 wherein the microorganism is cultivated in a culture medium at a pH of about 4.0 to 7.5 and a temperature of about 17° to 33° C.

6. A method according to claim 5 wherein the culture medium is Sabauroud dextrose broth, the pH is about 6.0 to 6.5 and the temperature is about 26° to 28° C.

7. A method according to any one of claims 1 to 6 wherein the weight ratio of biphenyl to dry cells of microorganism is no greater than 0.028 to 1.

* * * * *